United States Patent [19]
Anderson et al.

[11] Patent Number: 5,977,076
[45] Date of Patent: Nov. 2, 1999

[54] METHOD AND MATERIAL FOR INHIBITING COMPLEMENT

[76] Inventors: Byron E. Anderson, 5801 Reba, Morton Grove, Ill. 60053; Jonathan P. Fryer, 474 N. Lake Shore Dr., Chicago, Ill. 60611

[21] Appl. No.: 09/060,393

[22] Filed: Apr. 14, 1998

Related U.S. Application Data

[60] Provisional application No. 60/043,335, Apr. 14, 1997.

[51] Int. Cl.$^6$ .................................................. A61K 38/05
[52] U.S. Cl. .................................................. 514/19; 514/2
[58] Field of Search ................................. 514/19, 17, 18, 514/2

[56] References Cited

U.S. PATENT DOCUMENTS

| | | | |
|---|---|---|---|
| 3,941,763 | 3/1976 | Sarantakis | 260/112.5 |
| 4,546,082 | 10/1985 | Kurjan et al. | 435/172.3 |
| 4,588,684 | 5/1986 | Brake | 435/68 |
| 4,775,622 | 10/1988 | Hitzement et al. | 435/68 |
| 4,945,039 | 7/1990 | Suzuki et al. | 435/7 |
| 5,084,398 | 1/1992 | Huston et al. | 436/535 |
| 5,336,762 | 8/1994 | Ranney | 534/7 |
| 5,364,930 | 11/1994 | Baumann et al. | 530/326 |
| 5,773,569 | 6/1998 | Wrighton | 530/300 |

FOREIGN PATENT DOCUMENTS

WO 89/04675  6/1989  WIPO .............................. A61M 1/36

OTHER PUBLICATIONS

Burton et al., 1980, *Nature*, 288:338–44.
Ellman, 1959 *Arch. Biochem. Biophys.*, 82:70–77.
Kulkarni et al., 1981, *Cancer Res.*, 41:2700–06.
Takada, 1984, *Immunophamacology*, 8:27–35.
Bach et al., 1995, *Nature Medicine*, 1(9):869–873.
Bach et al., 1996, *Immunology Today*, 17(8):379–384.
Baldwin et al., 1995, *Transplantation*, 59(6):797–808.
Baumann et al., 1990, *J. Biol. Chem.*, 265(30):18414–22.
Blair et al., 1983, *J. Immunol. Methods*, 59:129–143.
Boackle et al., *Nature*, 282:742–743 (1979).
Brauer et al., *J. Immunol.*, 151:7240–7248 (1993).
Burton, 1985, Molec. Immunol., 22:161–206.
Burton, 1988, *Molec. Immunol.*, 25:1175–81.
Chou and Fasman, 1978, *Adv. Enzym.*, 47:45–148.
Comis et al., 1985, *Biochem. Biophys. Acta*, 842(1):45–51.
Cozzi et al., 1995, *Nature Medicine*, 1(9):964:966.
Davis et al., 1985, *Biochem. Int'l.*, 10:395–404.
DeGrado et al., 1981, *J. Am. Chem. Soc.*, 103:679–81.
Deisenhofer et al., 1978, *Hoppe–Seyler's Z. Physiol. Chem. Bd.*, 359:975–85.
Deisenhofer, 1981, *Biochemistry*, 20(9):2361–2370.
Duncan and Winter, 1988, *Nature*, 332:738–40.
Ellman, 1958, *Arch. Biochem. Biophys.*, 74:443–450.
Endo et al., 1983, *Ann. Clin. Biochem.*, 20:163–168.
Erlanger, 1980, *Methods in Enzymology*, 70:85–104.
Fields, 1972, *Meth. Enzymol.*, 25B:464–68.
Fryer et al., 1995, "Role of Macrophages in Delayed Vascular Xenograft Rejection," pp. 396–397, Surgical Forum, 81st Annual Clinical Congress 1995, vol. XLVI.

Fryer et al., 1995, *Transplantation*, 59(2):171–176.
Fryer, 1996, "Prolongation of Discordant Xenograft Survival by Inhibition of C1Q Deposition," Abstract for 15th Annual Scientific Meeting for the American Society of Transplant Physicians.
Fryer et al., Inhibition of Porcine Endothelial Cell Lysis by Human Serum Using Peptides Which Inhibit C1q Deposition, Abstract from May 1996 22nd Annual Scientific Meeting, American Society of Transplant Surgeons.
Fryer et al., Inhibition of Porcine Endothelial Cell Lysis by Human Serum Using Peptides Which Inhibit C1q Deposition, Abstract from Aug. 1996 XVI Int'l Congress of the Transplantation Society.
Fryer et al., Inhibition of Porcine Endothelial Cell Lysis by Human Serum Using Peptides Which Inhibit C1q Deposition, Abstract from Oct. 1996 IBC's Second Bi–Annual Symposium on Xeno Transplantation.
Garnier et al., 1978, *J. Molec. Biol.*, 120:97–120.
Gauthier et al., 1982, *J. Exp. Med.*, 156:766–77.
Ghebrehiwet et al., 1993,"The C1q–R Participates in Immunoregulation and Signal Transduction," *Behring Inst. Mitt.*, No. 93, pp. 236–240.
Guedson et al., 1979, *J. Histochem. Cytochem.*, 27(8):1131–39.
Henry (ed), *Clinical Diagnosis and Management by Laboratory Method* published 16th ed by W.B. Saunders, pp. 1425–1429 (1979).
Hughes–Jones and Gardner, 1978, *Immunology*, 34:459–63.
Jones et al., 1982, *J. Immunol. Meth.*, 53:201–208.
Jones, 1996, *Nature Biotechnology*, 14:698–700.
Kennedy, 1994, *Transplantation*, 57(10):1494–1501.
Lancet et al., 1978, *Biochem. Biophys. Res. Commun.*, 85(2):608–614.

(List continued on next page.)

*Primary Examiner*—Cecilia J. Tsang
*Assistant Examiner*—David Lukton
*Attorney, Agent, or Firm*—Sheridan Ross

[57] ABSTRACT

The invention provides a method of inhibiting complement in a mammal comprising administering to the mammal an effective amount of a carrier having coupled thereto a plurality of dipeptides selected from the group consisting of tryptophan-tyrosine, tyrosine-tryptophan and tryptophan—tryptophan. The invention further provides a method of prolonging the survival of tissue transplanted into a mammal comprising administering to the mammal an effective amount of a carrier having coupled thereto a plurality of dipeptides selected from the group consisting of tryptophan-tyrosine, tyrosine-tryptophan and tryptophan—tryptophan. The invention also provides a method of treating an inflammatory response in a mammal comprising administering to the mammal an effective amount of a carrier having coupled thereto a plurality of dipeptides selected from the group consisting of tryptophan-tyrosine, tyrosine-tryptophan and tryptophan—tryptophan. Finally, the invention provides a pharmaceutical composition comprising a carrier having coupled thereto a plurality of dipeptides selected from the group consisting of tryptophan-tyrosine, tyrosine-tryptophan and tryptophan—tryptophan in a pharmaceutically-acceptable vehicle.

8 Claims, 11 Drawing Sheets

OTHER PUBLICATIONS

Langone et al., 1982, *Adv. Immunol.*, 32:157–252.
Langone et al., 1978, *J. Immunol.*, 121(1):327–32.
Lukas et al., 1981, *J. Immunol.*, 127(6):2555–60.
Makowka et al., 1995, *Transplantation*, 59(12):1654–1659.
Marquart et al., 1980, *J. Mol. Biol.*, 141:369–91.
Marques et al., 1993, *J. Biol. Chem.*, 268(14):10393–10402.
Merrifield, 1963, *J. Am. Chem. Soc.*, 85:2149–54.
Moe and Kaiser, 1985, *Biochem.*, 24:1971–76.
One et al., 1969, *J. Thor. Cardiovas. Surg.*, 57:225–229.
Parker et al., 1996, *Immunology Today*, 17(8):373–378.
Prystowsky et al., 1981, *Biochemistry*, 20:6349–56.
Reid, 1979, *Biochemical J.*, 179:367–71.
Reid et al., 1982, *Biochemical J.*, 203:559–69.
Romanella et al., 1997, *Transplantation*, 63(7):1021–1025.
Ryan, 1995, *Nature Medicine*, 1(9):967–968.
Schaapherder et al., 1994, *Transplantation*, 57(9):1376–1382.
Schaff et al., 1983, *J. Thor. Cardiovas. Surg.*, 85:434–439.
Seller et al., 1991, *Biochem. J.*, 274:481–490.
Siegel et al., 1983, *Clin. Exp. Immunol.*, 52:157–163.
Stålenheim et al., 1973, *Immunochem.*, 10:501–507.
Takada, 1985, *Immunopharmacology*, 9:87–95.
Taylor et al., 1982, *Mol. Pharmacol.*, 22:657–66.
Theofilopoulos et al., 1979, *Adv. Immunol.*, 28:89–220.
Theofilopoulos et al., *Immunodiagnostics of Cancer*, p. 896(M. Decker Inc., New York, NY 1979).
Travis, 1995, *Science News*, 148:298–301.
Veerhuis et al., 1985, *Eur. J. Immunol.*, 15:881–887.
White, Xeno, 4(3):50–54 (1996).
Zubler et al., 1976, *J. of Immunol.*, 116(1):232–235.

METHOD AND MATERIAL FOR INHIBITING COMPLEMENT

This application claims benefit of provisional application 60/043,335, filed Apr. 14, 1997.

FIELD OF THE INVENTION

This invention relates to a method of inhibiting complement. In particular, the invention relates to a method of inhibiting complement to prolong the survival of tissues transplanted into a mammal or to treat an inflammatory response in a mammal. The inhibition of complement is accomplished by administering an effective amount of a carrier, such as bovine serum albumin or dextran, having coupled thereto a plurality of dipeptides selected from the group consisting of tryptophan-tyrosine, tyrosine-tryptophan and tryptophan—tryptophan.

BACKGROUND OF THE INVENTION

Xenotransplants are typically rejected within minutes to hours in untreated recipients. This early rejection is called hyperacute rejection and results from recipients having preexisting xenoreactive natural antibodies which bind to antigens of the endothelial cells of the donor organ, thereby activating the complement cascade. This ultimately results in the formation of a membrane attack complex which activates the endothelial cells or penetrates the cell membrane, resulting in cell death and necrosis of the xenograft. The activation of endothelial cells is devastating, resulting in thrombosis, inflammation and rejection of the transplanted tissue.

Thus, complement activation plays a major role in the pathogenesis of hyperacute rejection of xenografts, and several strategies for combating hyperacute rejection have been developed which are aimed at preventing activation of the complement cascade, including the production of transgenic pigs capable of expressing genes for human complement regulatory proteins on organs intended for transplantation into humans (*Nature Medicine*, 1, 869–873, 1995). These strategies, the role of complement, and hyperacute rejection have recently been reviewed (Cozzi and White, *Nature Medicine*, 1, 964–6, 1995; Ryan, *Nature Medicine*, 1, 967–8, 1995; Parker, et al., *Immunology Today*, 17, 373–378, 1996; White, *Xeno*, 4, 46–49, 1996).

These strategies can prevent immediate graft loss associated with hyperacute rejection, but a delayed xenograft rejection (or acute vascular rejection) still occurs a few days later (Hancock and Bach, *Xeno*, 2, 68–72, 1994) in which, the evidence indicates, antibody-dependent cell-mediated cytotoxicity plays a prominent role (Baldwin, et al., *Transplantation*, 59, 797–808, 1995; Schaapherder, et al., *Transplantation*, 57, 1376–82, 1994). In many of the strategies designed to block hyperacute rejection, the complement cascade is regulated at the level of C3 or at more distal points, so that deposition of the early binding components (C1q, C1r, C1s, C2, C4) still proceeds. Also, with any of the strategies, C1q will still bind to certain immunoglobulins (Igs), especially IgM and the IgG1 and IgG3 subclasses in humans. Thus, C1q (C1) binds with activation of C1, C2 and C4, and these early complement components are capable of producing changes characteristic of delayed xenograft rejection. Furthermore, many immunocompetent cells which play a role in rejections, such as monocytes, macrophages, platelets, neutrophils and B lymphocytes, bind to C1q bound to the graft through C1q receptors expressed on their surfaces (Baldwin et al., *Transplantation*, 59, 797–808, 1995). Many of the cellular events triggered by these interactions can be harmful to the graft (Fryer, et al., *Surgical Forum*, 46, 396–7, 1995; Ghebrehiwet, B. et al., *Behring Inst. Mitt.*, 93, 236–240, 1993).

Hyperacute rejection and acute rejection of allografts occur in recipients having preexisting antibodies which bind to antigens of the graft, particularly to histocompatibility antigens. Hyperacute and acute rejection occur by mechanisms analogous to those seen in xenograft rejection discussed above, including C1q binding to antibodies deposited on the graft resulting in complement activation and the binding of immunocompetent cells to C1q. See Baldwin et al., *Transplantation*, 59, 797–808 (1995). C1q-mediated processes are possibly involved in chronic rejection of allografts, as well. See id.

Inflammation in some diseases, such as rheumatoid arthritis, has been associated with the deposition of immune complexes in tissues and the activation of the complement cascade. The binding of C1q to immune complexes deposited in the tissues initiates the complement cascade, and the action of the complement components, alone or concurrently with other biologic molecules, ultimately leads to tissue damage. The binding of immunocompetent cells to C1q at sites of inflammation may also be involved in inflammatory processes.

It has previously been shown that a peptide derived from C1q could inhibit C1q binding to immunoglobulin (Baumann, M A and Anderson, B E, *J. Biol. Chem.*, 265, 18414–22, 1990; U.S. Pat. No. 5,364,930). It was also found that this peptide could inhibit complement activation and prolong graft survival in an animal model (guinea pig heart to C6 deficient PVG rat model) (Baumann, M A, Anderson, B E and Fryer, J P, "A Synthetic Peptide and its Uses", U.S. patent application Ser. No. 08/628,383, filed, Apr. 5, 1996).

C1q binds to the CH2 domain of IgG, and several sequences of the CH2 domain are potentially involved (Duncan, A R, Winter, G, *Nature*, 332, 738–9, 1988; Lubias, T J, Munoz, H, Erickson, B W, *J. Immunol.*, 127, 2555–60, 1981; Boackle, R J Johnson, B J, Caughman, G B, *Nature*, 282, 742–3, 1979). Takada et al. (Takada, A, Shirahama, S, Takada, Y. *Immunopharmacology*, 9, 87–95, 1985) showed that peptides containing the sequence tryptophan-tyrosine (Trp-Tyr) and Trp-Tyr itself could inhibit complement activation. The Trp-Tyr sequence corresponds to residues 277–278 of the IgG CH2 domain.

SUMMARY OF THE INVENTION

The invention provides a method of inhibiting complement in a mammal. The method comprises administering to the mammal an effective amount of a carrier having coupled thereto a plurality of dipeptides selected from the group consisting of tryptophan-tyrosine, tyrosine-tryptophan and tryptophan—tryptophan (hereinafter "dipeptide-carrier").

The invention further provides a method of prolonging the survival of tissue transplanted into a mammal. The method comprises administering to the mammal an effective amount of a dipeptide-carrier of the invention.

The invention also provides a method of treating an inflammatory response in a mammal. The method comprises administering to the mammal an effective amount of a dipeptide-carrier of the invention.

Finally, the invention provides a pharmaceutical composition. The composition comprises a dipeptide-carrier of the invention in a pharmaceutically-acceptable vehicle.

DETAILED DESCRIPTION OF THE PRESENTLY PREFERRED EMBODIMENTS

Figure 1:
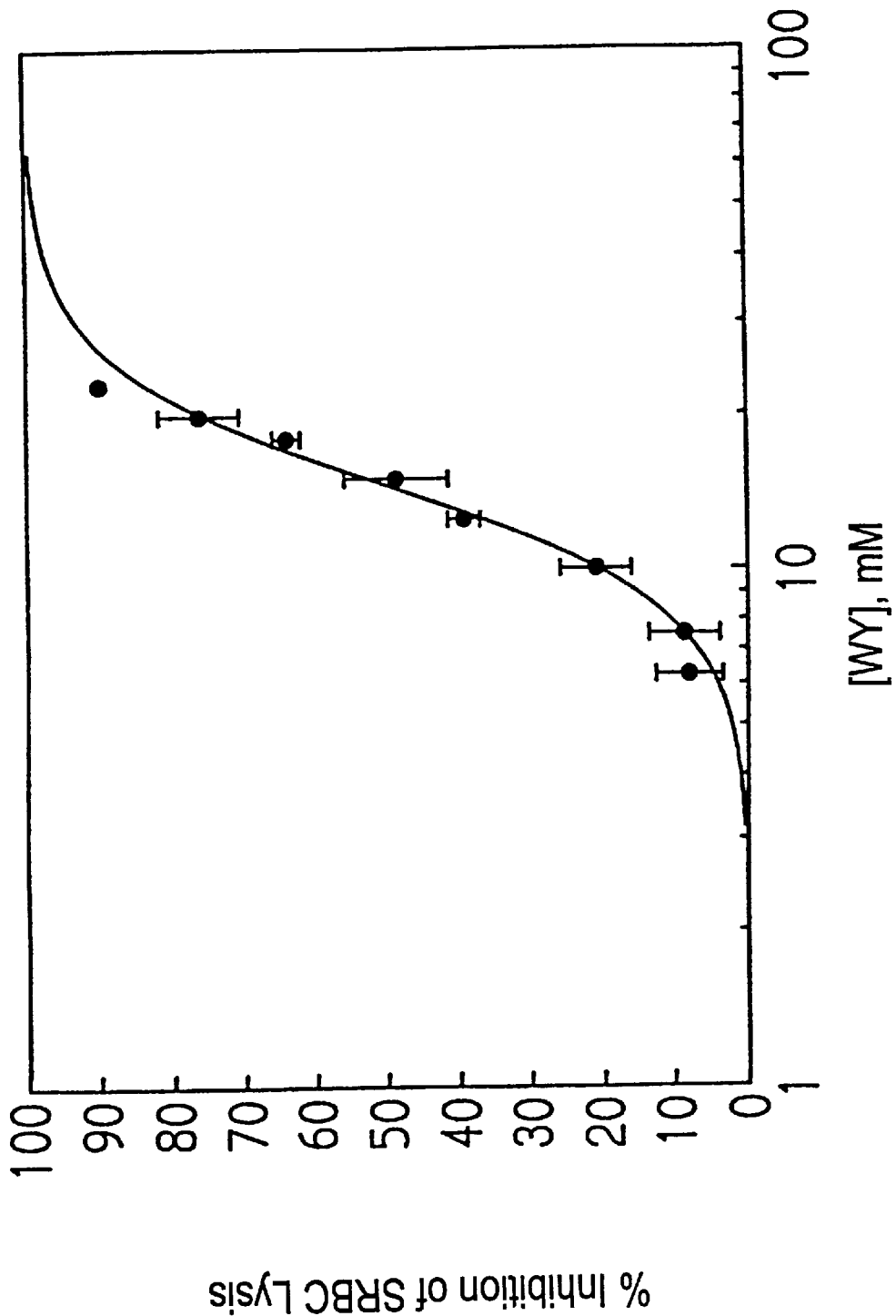
FIG. 1. Graph of inhibition of sheep red blood cell (SRBC) lysis versus concentration of the dipeptide Trp-Tyr ([WY]). The data points are the averages of three assays performed at different times ±SD values.

The dipeptides can be made in a variety of ways. For instance, solid phase synthesis techniques can be used. Suitable techniques are well known in the art, and include those described in Merrifield, in *Chem. Polypeptides*, pp. 335–61 (Katsoyannis and Panayotis eds. 1973); Merrifield, *J. Am. Chem. Soc.*, 85, 2149 (1963); Davis et al., *Biochem. Int'l*, 1, 10, 394–414 (1985); Stewart and Young, *Solid Phase Peptide Synthesis* (1969); U.S. Pat. No. 3,941,763; Finn et al., in *The Proteins*, 3rd ed., vol. 2, pp. 105–253 (1976); and Erickson et al. in *The Proteins*, 3rd ed., vol. 2, pp. 257–527 (1976). Dipeptides are also available commercially from, e.g., Sigma Chemical Co. (St. Louis, Mo.), Bachem Bioscience, Inc. (King Of Prussia, Pa.), and Peptides International (Louisville, Ky.). The dipeptides may comprise D-amino acids or L-amino acids.

The dipeptides are covalently coupled to a carrier. Suitable carriers will have a multiplicity of sites to which the dipeptides can be coupled. Such carriers include proteins, polypeptides, carbohydrates, polysaccharides, lipopolysaccharides, and nucleic acids. Suitable proteins include albumins (e.g., bovine serum albumin, ovalbumin, human serum albumin), immunoglobulins, thyroglobulins (e.g., bovine thyroglobulin), and hemocyanins (e.g., Keyhole Limpet hemocyanin). Suitable polypeptides include polylysine and polyalaninelysine. Suitable polysaccharides include dextrans of various sizes (e.g., 12,000 to 500,000 molecular weight).

The dipeptides are covalently coupled to the carrier using methods and agents well known in the art. Suitable agents include gluteraldehyde, carbodiimide, cyanoborohydride, diimidoesters, periodate, alkylhalides, succinimides, dimethylpimelimidate and dimaleimides. See Example 1; Blait, A. H., and Ghose, T. I., *J. Immunol. Methods*, 59:129 (1983); Blair, A. H., and Ghose, T. I., *Cancer Res.*, 41:2700 (1981); and Gauthier, et al., *J. Exp. Med.*, 156:766–777 (1982). See also *Catalog And Handbook* (1994–1995) and *Products Catalog* (1997), Pierce Chemical Co., Rockford, Ill., for a list of possible coupling agents. Additional references concerning carriers and techniques for coupling dipeptides thereto are: Erlanger, *Methods In Enzymology*, 70, 85–104 (1980); Makela and Seppala, *Handbook of Experimental Immunology* (Blackwell 1986); Parker, *Radioimmunoassay of Biologically Active Compounds* (Prentice-Hall 1976); Butler *J. Immunol. Meth.*, 7, 1–24 (1974); Weinryb and Shroff, *Drug. Metab. Rev.*, 10, 271–83 (1979); Broughton and Strong, *Clin. Chem.*, 22, 726–32 (1976); Playfair et al., *Br. Med. Bull.*, 30, 24–31 (1974).

Determining sufficient and optimum conditions for coupling the dipeptides to the carriers is well within the skill in the art. For instance, see Example 1. In this regard, an important factor is the ratio of the dipeptide to the carrier. For instance, it has been found that a ratio (weight/weight)

of dipeptide:carrier of at least 1:1 is necessary to achieve sufficient coupling of Trp-Tyr dipeptides to dextran to produce Trp-Tyr-Dextrans having high levels of activity (see Example 1). Another important factor may be the number of chemical coupling groups of the carrier. For example, it has been found the a ratio (weight/weight) of periodate:dextran of 4:1 produced Trp-Tyr-Dextrans having higher levels of activity than lower ratios (see Example 1).

The dipeptides may be attached to the carrier by means of a spacer arm which allows the dipeptide to be spaced away from the surface of the carrier so that it can better interact with C1q. Suitable spacer arms are well known in the art and include aliphatic chains which terminate in a functional group such as amino, carboxyl, thiol, hydroxyl, aldehyde, or maleimido, which is active in a coupling reaction (see above). For instance, the spacer arm may be a diamine, an amino acid, or a peptide containing less than ten amino acids, preferably two to three amino acids. Spacers are also inherent to many coupling agents (see *Catalog And Handbook* (1994–1995) and *Products Catalog* (1997), Pierce Chemical Co., Rockford, Ill.). The spacer arm may be located on the carrier, on the dipeptide, on both, or in the coupling agent.

The dipeptide-carriers can be used to inhibit complement in a mammal. "Inhibit complement" is used herein to mean that the dipeptide-carriers inhibit the binding of C1q to immunoglobulins (thereby inhibiting complement activation and the complement cascade at the site of C1q-immunoglobulin binding), to C1q receptors on cells, or both. “Inhibit” is used herein to mean reduce or prevent. Thus, the dipeptide-carriers can be used to treat any condition or disease where C1(C1q) binding to immunoglobulin or cells contributes to the condition or disease.

For instance, the dipeptide-carriers can be used to treat inflammation. “Treat” is used herein to mean that the inflammatory response is reduced or prevented. As noted above, inflammation in some diseases has been associated with the deposition of immune complexes in tissues and the activation of the complement cascade. It is the binding of C1q to immune complexes deposited in the tissues which initiates the complement cascade, and the action of the complement components, alone or concurrently with other biologic molecules, ultimately leads to tissue damage. Accordingly, a dipeptide-carrier according to the invention can be administered to a mammal suffering from inflammation mediated by the classical complement pathway to inhibit the binding of immune complexes by C1q and, thereby, reduce or prevent tissue damage and further inflammation. Inflammatory diseases that can be treated include autoimmune diseases (such as rheumatoid arthritis). Also, the inflammation associated with bacterial or viral infections can be treated.

The dipeptide-carriers can also be used to prolong the survival of tissue transplanted into a mammal. As noted above, rejection of both xenografts and allografts involves the binding of C1q to antibodies deposited on the graft, thereby initiating activation of the complement cascade, and binding of C1q to the C1q receptors of immunocompotent cells involved in graft rejection. Accordingly, a dipeptide-carrier of the invention administered to an animal receiving a tissue transplant will prolong the survival of the graft by inhibiting the binding of C1q to antibodies and cells involved in graft rejection and by inhibiting complement activation and the complement cascade. In particular, the dipeptide-conjugates of the invention have been found to significantly prolong xenograft survival. For instance, in a rat model of delayed xenograft rejection, xenograft survival was prolonged from 1.4±0.5 days in controls to 2.4±0.7 days in treated animals (p=0.009).

Effective dosage forms, modes of administration and dosage amounts of the dipeptide-carriers of the invention may be determined empirically, and making such determinations is within the skill of the art. It is understood by those skilled in the art that the dosage amount will vary with the particular dipeptide-carrier employed, the condition being treated, the severity of the condition, the route of administration, the rate of excretion, the duration of the treatment, the identity of any other drugs being administered to the mammal, the age, size and species of the mammal, and like factors well known in the medical and veterinary arts. In general, a suitable daily dose of a compound of the present invention will be that amount which is the lowest dose effective to produce a therapeutic effect. However, the total daily dose will be determined by an attending physician or veterinarian within the scope of sound medical judgment. If desired, the daily dose may be administered in multiple sub-doses, administered separately at appropriate intervals throughout the day.

The dipeptide-carriers of the present invention may be administered to an animal patient for therapy by any suitable route of administration. Preferably, they administered parenterally (e.g., intravenously, intraperitoneally, subcutaneously, or intramuscularly).

For treating graft rejection, the compositions are preferably administered intravenously. They may be administered before, during, and/or after the transplant operation. For treating inflammation, the compositions are preferably administered intravenously or injected at the site of inflammation.

The pharmaceutical compositions of the invention comprise a dipeptide-carrier of the invention as an active ingredient in admixture with one or more pharmaceutically-acceptable vehicles and, optionally, with one or more other compounds, drugs or other materials. Each vehicle must be “acceptable” in the sense of being compatible with the other ingredients of the formulation and not injurious to the patient. Such vehicles are well known in the art, as are methods of preparing pharmaceutical compositions.

Pharmaceutical compositions of the invention suitable for parenteral administrations comprise one or more dipeptide-carriers of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient, or suspending or thickening agents.

Examples of suitable aqueous and nonaqueous vehicles which may be employed include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption, such as aluminum monosterate and gelatin, or by dissolving or suspending the dipeptide-carrier (s) in an oil vehicle.

The formulations may be presented in unit-dose or multi-dose sealed containers (for example, ampoules and vials).

EXAMPLES

Example 1
Inhibition of Complement-Mediated Lysis By Trp-Try-BSA and Trp-Tyr-Dextran This example describes the inhibition of complement-mediated lysis in two different systems by carriers having tryptophan-tyrosine (Trp-Tyr) dipeptides coupled to them (Trp-Tyr-Carrier). In particular, inhibition of complement activation was obtained in a sheep red blood cell (SRBC) lysis assay using conjugates of Trp-Tyr covalently coupled to bovine serum albumin (Trp-Tyr-BSA) and to several sizes of dextran (Trp-Tyr-Dextran). The conjugates inhibited complement activation consistently and at low weight amounts of the Trp-Tyr-BSA or Trp-Tyr-Dextran and at low Trp-Tyr concentrations (concentrations of Trp-Tyr in the conjugates, not free Trp-Tyr, see below). Trp-Tyr-BSA and Trp-Tyr-Dextran conjugates also inhibited the complement-mediated lysis of porcine endothelial cells (PECS) by human serum as the source of anti-PEC antibody and complement.

The formulations may be stored in a lyophilized condition requiring only the addition of the sterile liquid carrier, for example water for injection, immediately prior to use.

A. Sheep Red Blood Cell Lysis

To perform this assay, sheep erythrocytes (SRBCs) are "sensitized" by the addition of anti-SRBC antibody. Addition of serum as a source of complement results in C1 binding and activation of the complement system with resultant lysis of the erythrocytes. The released hemoglobin is measured spectrophotometrically and is related to the amount of complement activation.

SRBCs were purchased from BioWhittaker, Walkersville, Md. They were diluted to 0.28% cells/ml in Tris-buffer saline containing gelatin [TBSG, 50 mM Tris-HCl (Mallinckrodt Specialty Chemicals Co., Paris, Ky.) and 150 mM NaCl (Aldrich Chemical Co., Milwaukee, Wis.) plus 2% swine gelatin (Type 1, Sigma Chemical Co., St. Louis, Mo.)].

Hemolysin reagent (anti-sheep erythrocyte stromata serum) was purchased from BioWhittaker, Walkersville, Md. It was diluted 1:400 in TBSG.

Human serum was used as the source of complement. Blood was drawn from a volunteer into 6 ml Vacutainer brand serum separation tubes (Becton Dickinson, Franklin Lakes, N.J.) and the serum was separated by centrifugation at 1500×g for 10 min at room temperature. Serum was stored in small aliquots at −70° C. The serum was titered for complement activity by using serial dilutions in TBSG added to SRBCs and hemolysin. A serum dilution was used in subsequent assays that gave between 40–80% of total SRBC lysis.

The diluted SRBCs (50 μl) were added to wells of a Corning 96-well, flat bottomed, polystyrene, non-coated plate (Corning Glass Works, Corning, N.Y.). Then, 50 μl of diluted hemolysin was added, followed by 50 μl of various inhibitors. The well contents were gently mixed using a multichannel pipette, and the plate was incubated for 30 min at 37° C. The diluted serum (50 μl) was added to the mixture of SRBCs, hemolysin and inhibitors, and each well was gently mixed. The plate was incubated for 60 min at 37° C. The plate was then centrifuged at 500×g at room temperature for 5 min, after which 100 μl of supernatant was removed from each well and transferred to another 96-well Corning plate. The relative amounts of hemoglobin were quantitated at 405 nm using a Coulter Microplate Reader (Hialeah, Fla.). Total cell lysis was determined by pipetting an aliquot of the stock SRBCs into 200 μl of $H_2O$, removing 100 μl of supernatant and determining the OD at 405 nm.

Total complement activity of the diluted human serum was calculated as the OD at 405 nm of human serum without any additions minus OD at 405 nm of an incubation mixture without human serum or with heat-inactivated human serum (treated for 1 hour at 56° C). The percent inhibition obtained with various inhibitor substances was calculated as the total complement activity (100%) minus the percent complement activity in the presence of inhibitor. All assay points were determined in duplicate or triplicate. In some cases, as noted below, data of different conjugates, or of assays performed at different times, were combined and the results averaged and plotted as the average ±SD.

B. Porcine Endothelial Cell Lysis Assay

Culture plates (Falcon 24 well plates, Becton Dickinson, Lincoln Park, N.J.) were coated by addition of 0.5 ml/well of 2% gelatin (Type B, from bovine skin, Sigma Chemical Co., St. Louis, Mo.) diluted 1:10 in Hanks buffered salt solution (Gibco BRL, Grand Island, N.Y.), followed by incubation for 15 min at room temperature. The gelatin solution was removed, and $125 \times 10^3$ pig aorta endothelial cells (PAECs, Cell Systems, Kirland, Wash.) in 2 ml of cell culture medium (CCM, Dulbecco's modified Eagle's medium (DMEM) with high glucose (Gibco BRL) containing 20% defined fetal bovine serum (FBS, HyClone Laboratories, Logan, Utah) that had been heat-inactivated for 30 min. at 56° C., 1%(v/v) L-glutamine (200 mM, Gibco BRL) and penicillin G sodium (10,000 units/ml)/ streptomycin sulfate (10,000 μg/ml in 0.85% saline, Gibco BRL)) were added per well. The plate was centrifuged in a model GS-6R Beckman table top centrifuge at 20×g for 2 min with the brake off to settle the cells onto the gelatin in an even monolayer, after which the plate was incubated at 37° C. in 5% $CO_2$—95% air. After 4 hours, cell attachment had occurred, and the CCM was removed and replaced with 2 ml of fresh CCM. In 2–4 days the PAECs had grown to 80–100% confluence and were used in the complement mediated chromium release assay.

The PAECs were washed 3 times with 1 ml of serum free medium (SFM). The plate was drained on paper towels between washes to remove as much medium as possible. Chromium radioisotope ($^{51}Cr$, $NaCrO_4$, Amersham Corp., Arlington Heights, Ill.) was diluted in SFM to give 40 μCi/ml and 100 μl was added to each well of the PAEC culture plate and the plate was incubated for 2 hours at 37° C. under 5% $CO_2$—95% air. The wells were washed three times with 1 ml of SFM, and then 1 ml of PBS was added to each well and incubation at 37° C. was continued for 30 min to help reduce $^{51}Cr$ background.

The various peptide inhibitors were diluted in SEM and 100 μl volumes/well preincubated with the PAECs at 37° C. for 30 min. 200 μl SEM was then added to each well, followed by the addition of 100 μl of undiluted human serum. Triplicate controls were done using 400 μl SEM to measure any spontaneous $^{51}Cr$ release, 400 μl 5% Triton X-100 to measure total lysis and 100 μl non-heat-inactivated undiluted human (HS) serum plus 300 μl SFM to measure total lysis by complement in a particular serum, and 100 μl heat-inactivated undiluted human serum (HI-HS) plus 300 μl SFM to measure background lysis when complement has been removed by heat-inactivation. The plate was incubated at 37° C. for 1 hour. Supernatant (200 μl) was removed from each well and added to 200 μl of scintillation cocktail (OptiPhase 'Supermix', Wallac, Inc., Turku, Finland) previously added to each well of a 24-well polyethylene terephtalate reading plate (Wallac, Inc.) and the plate was sealed with an acetate plate sealer (Dynatech Laboratories, Chantilly, Va.). The reading plate was placed on a shaker until the mixture appeared homogeneous. Radioactivity (CPMS) of the wells was counted for 2 min using the 1450 MicroBeta PLUS plate reader (Wallac, Inc.).

Total complement mediated lysis was determined from wells treated with HS alone and background counts were determined from wells treated with HI-HS alone. The average background was subtracted from all well counts and percent of inhibition calculated as total lysis minus lysis with inhibitor/total lysis and multiplying by 100. All experimental points were obtained in triplicate, and the data were plotted and analyzed in the same manner as the data from the SRBC assays.

C. Preparation of Trp-Tyr-BSA Conjugates

BSA (Sigma Chemical Co.) was dissolved to a concentration of 10 mg/ml in PBS (phosphate buffered saline, 0.12 M NaCl, 2.7 mM KCl, 10 mM Na phosphate, pH 7.4). To the BSA solution, solid $NaCNBH_3$ (Sigma) was added to a weight ratio of $NaCNBH_3$:BSA of 2:1. Glutaraldehyde (50%, Eastman Kodak Co., Rochester, N.Y.) was then added slowly to the BSA solution in a volume ratio of 1 part glutaraldehyde to 5 parts BSA solution. Insoluble material was seen to rapidly form. The mixture was stirred and allowed to react for 16 hours at room temperature. The mixture was then dialyzed in 12,000–14,000 molecular weight cut off dialysis tubing (Spectra/Por, Baxter Diagnostics, McGaw Park, Ill.) against several changes of distilled water over 24 hours. Trp-Tyr (obtained from Sigma Chemical Co., St. Louis, Mo. or Bachem Bioscience, Inc., King of Prussia, Pa.) was dissolved in 0.1 M $K_2HPO_4$ to a concentration of 10 mg/ml, and an amount of Trp-Tyr added to the dialyzed BSA solution to give a 2:1 weight ratio of Trp-Tyr:BSA. In one set of experiments, the ratios of Trp-Tyr:BSA were varied. $NaCNBH_3$ was dissolved to a concentration of 40 mg/ml in 0.1 M $K_2HPO_4$ and was added to the BSA solution in a weight ratio of 1:5, $NaCNBH_3$:BSA. The mixture was left stirring for 16 hours at room temperature at which time the cloudy solution was changed to a clear solution. The mixture was dialyzed in 12,000–14,000 molecular weight cut off dialysis tubing against several changes of distilled water over at least 24 hours time. The retentate was lyophilized, then redissolved in about 1/10 the original volume either in PBS or water. The optical density at 280 nm of an aliquot of the solution diluted appropriately was obtained and the concentration of Trp-Tyr calculated using a determined extinction coefficient of Trp-Tyr of 18 OD units/mg Trp-Tyr/ml. The concentration of BSA was calculated on the basis that an insignificant amount of the starting material was lost throughout the conjugation procedure.

D. Preparation of Trp-Tyr-Dextran Conjugates

Dextrans of various sizes were obtained from Sigma and are designated corresponding to the average molecular weights of the dextran polymers: Dex 500 (500,000 average molecular weight), Dex 260 (260,000), Dex 167 (167,000), Dex 77 (77,000), Dex 41.6 (41,600), Dex 17 (17,000) and Dex 12 (12,000).

Sodium metaperiodate ($NaIO_4$, Sigma) was dissolved in water to a concentration of 1 g/10 ml and dextran was dissolved in water to a concentration of 1 g/20 ml. The two were combined at a weight ratio of 4:1 of $NaIO_4$:dextran and left to react with stirring for 16 hours at room temperature. The solution was dialyzed in 12,000–14,000 molecular weight cut off tubing over at least a 6-hour time period against several changes of $H_2O$. Trp-Tyr was dissolved to a concentration of 150 mg/ml in a 0.1 M $K_2HPO_4$ and $NaCNBH_3$ to a concentration of 80 mg/ml in 0.1 M $K_2HPO_4$. The reactants were mixed to achieve weight ratios of dextran:Trp-Tyr:$NaCNBH_3$ of 2:1:2.4 and allowed to react with stirring for 16 hours at room temperature. $NaBH_4$ (Sigma) dissolved to a concentration of 100 mg/ml in $H_2O$ was then added to a weight amount equal to 2 times the dextran and the mixture left stirring for an additional 16–24 hours at room temperature. The solution was then dialyzed, concentrated by lyophilization and the amounts of Trp-Tyr and dextrans determined as described above for the Trp-Tyr-BSA conjugates.

E. Results Takada et al. (Takada, A, Shirahama, S and Takada, Y, *Immunopharmacology*, 9, 87–95, 1985) showed that the diaromatic peptide, Trp-Tyr, and small peptides containing the Trp-Tyr sequence, inhibited complement activation in the range of about 1–10 mM using several types of assays. In the SRBC assay used here, Trp-Tyr inhibited human serum complement-mediated lysis of the SRBCs 20% at 10 mM concentration, 50% at 15 mM and nearly complete inhibition at the highest concentration of Trp-Tyr used (24 mM) (see FIG. 1).

Considering that C1q has six globular heads, each with one or more binding site(s) for immunoglobulin, it was hypothesized that a multimer of Trp-Tyr could bind to more than one globular head of C1q and, thus, be a more effective inhibitor of C1 binding to immunoglobulin. Therefore, conjugates of Trp-Tyr coupled to BSA and to dextrans of different sizes were produced and tested for their complement inhibiting activities.

Using a weight ratio of Trp-Tyr:BSA in the conjugation reaction of approximately 4:1 yielded a conjugate with 40.8 Trp-Tyr dipeptides per BSA molecule. Using a weight ratio of Trp-Tyr:BSA of approximately 2:1 yielded a conjugate with 41.5 Trp-Tyr dipeptides per BSA molecule. Finally, using a weight ratio of Trp-Tyr:BSA of approximately 1:1 yielded a conjugate with 12.4 Trp-Tyr dipeptides per BSA molecule.

Figure 2:
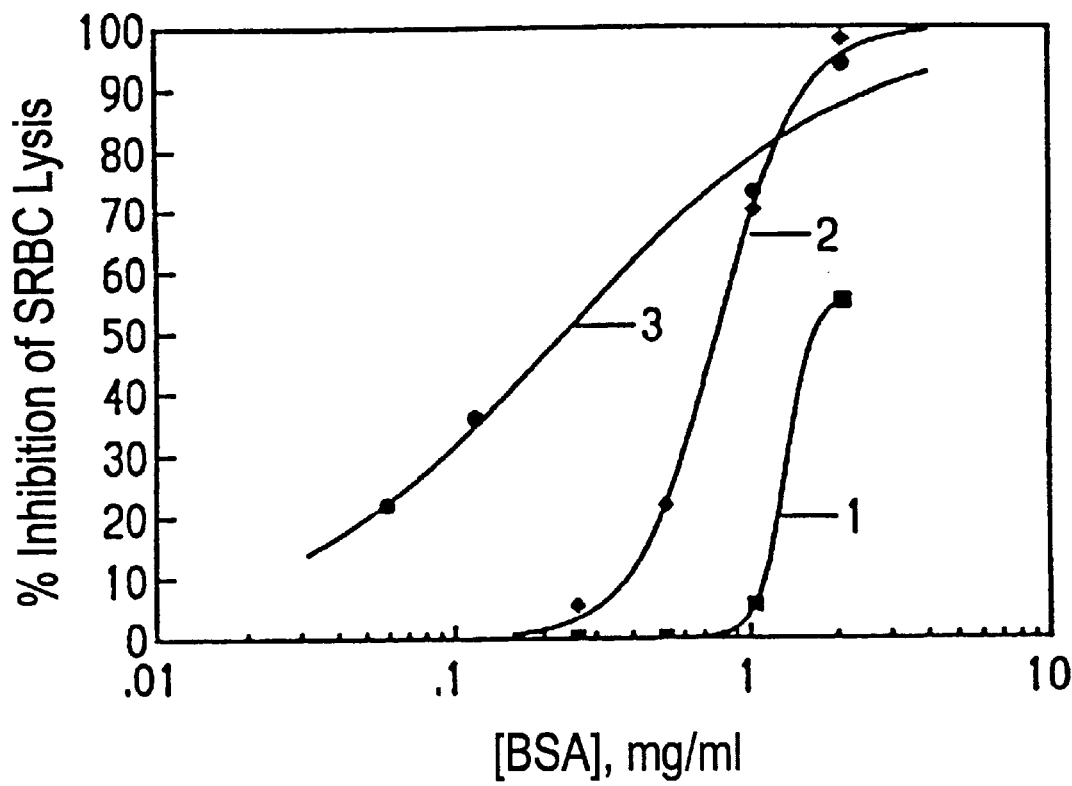
FIGS. 2A–B: Graphs of inhibition of SRBC lysis using Trp-Tyr conjugated to bovine serum albumin (BSA) versus concentration of Trp-Tyr-BSA ([BSA]) (FIG. 2A) and versus concentration of Trp-Tyr ([WY]) in the Trp-Tyr-BSA conjugate (FIG. 2B). The data points are averages of duplicates of a single assay. Curves 1, 2 and 3 are Trp-Tyr-BSA conjugates prepared using 1:1, 2:1 and 4:1 ratios, respectively, of Trp-Tyr to BSA in the reductive amination step.
Figure 2:
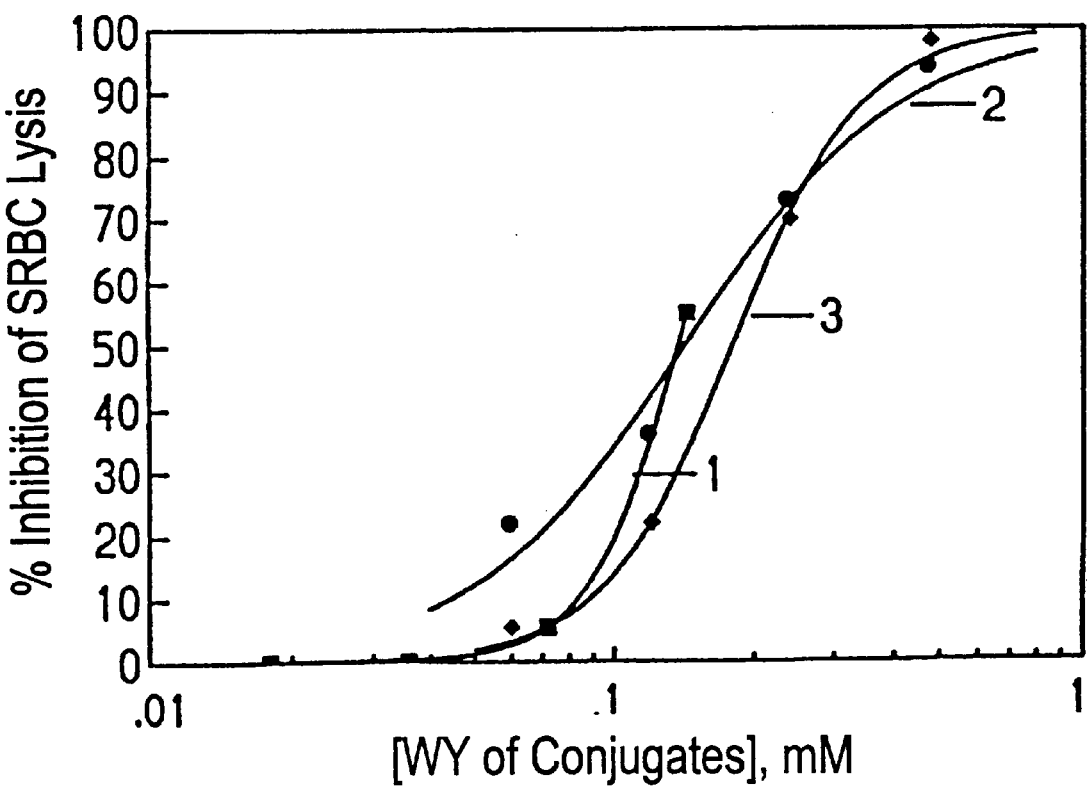
Figure 3:
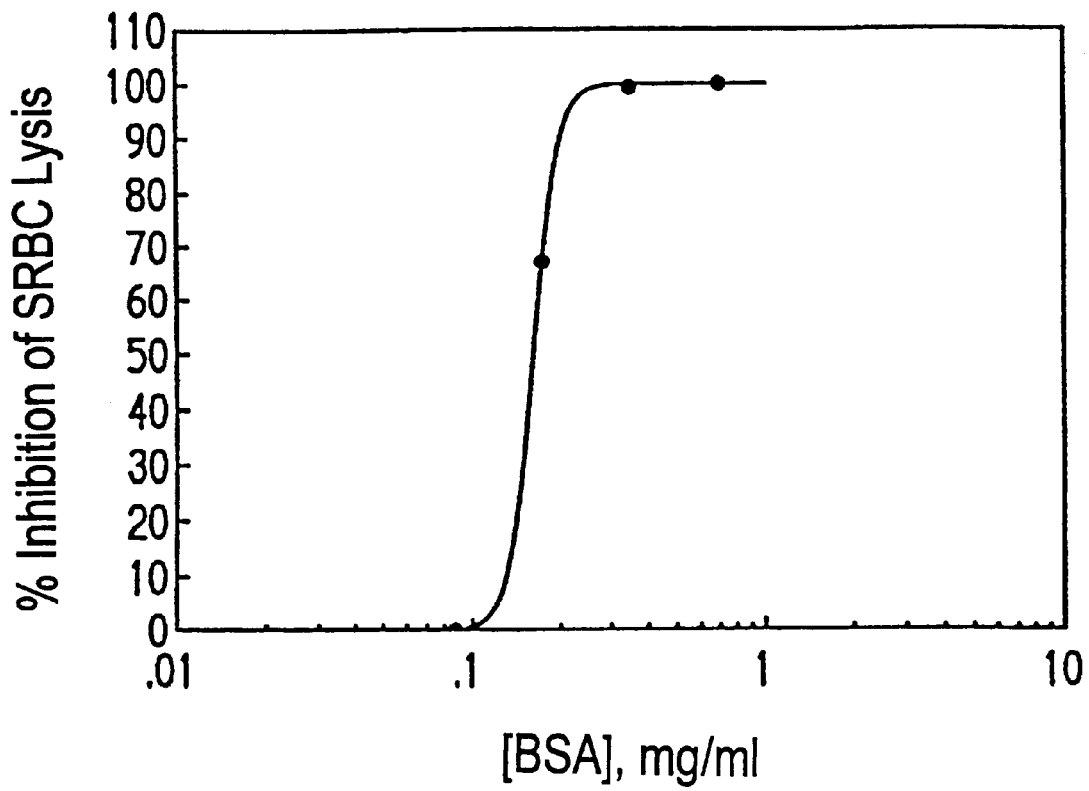
FIGS. 3A–B. Graphs of inhibition of SRBC lysis using a Trp-Tyr-BSA conjugate versus concentration of Trp-Tyr-BSA ([BSA]) (FIG. 3A) and versus concentration of Trp-Tyr ([WY]) in the Trp-Tyr-BSA conjugate (FIG. 3B). The data points are averages of duplicates of a single assay of. a Trp-Tyr-BSA preparation prepared using a ratio of Trp-Tyr:BSA of 2:1 in the reductive amination reaction.
Figure 3:
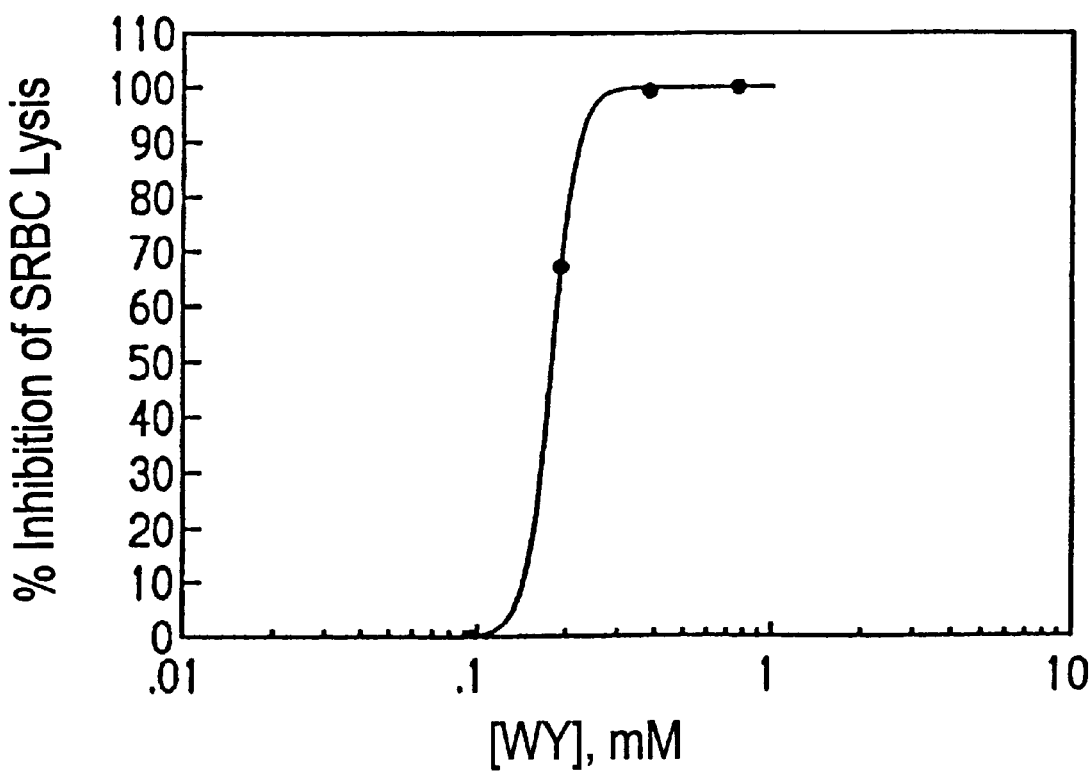
Figure 4:
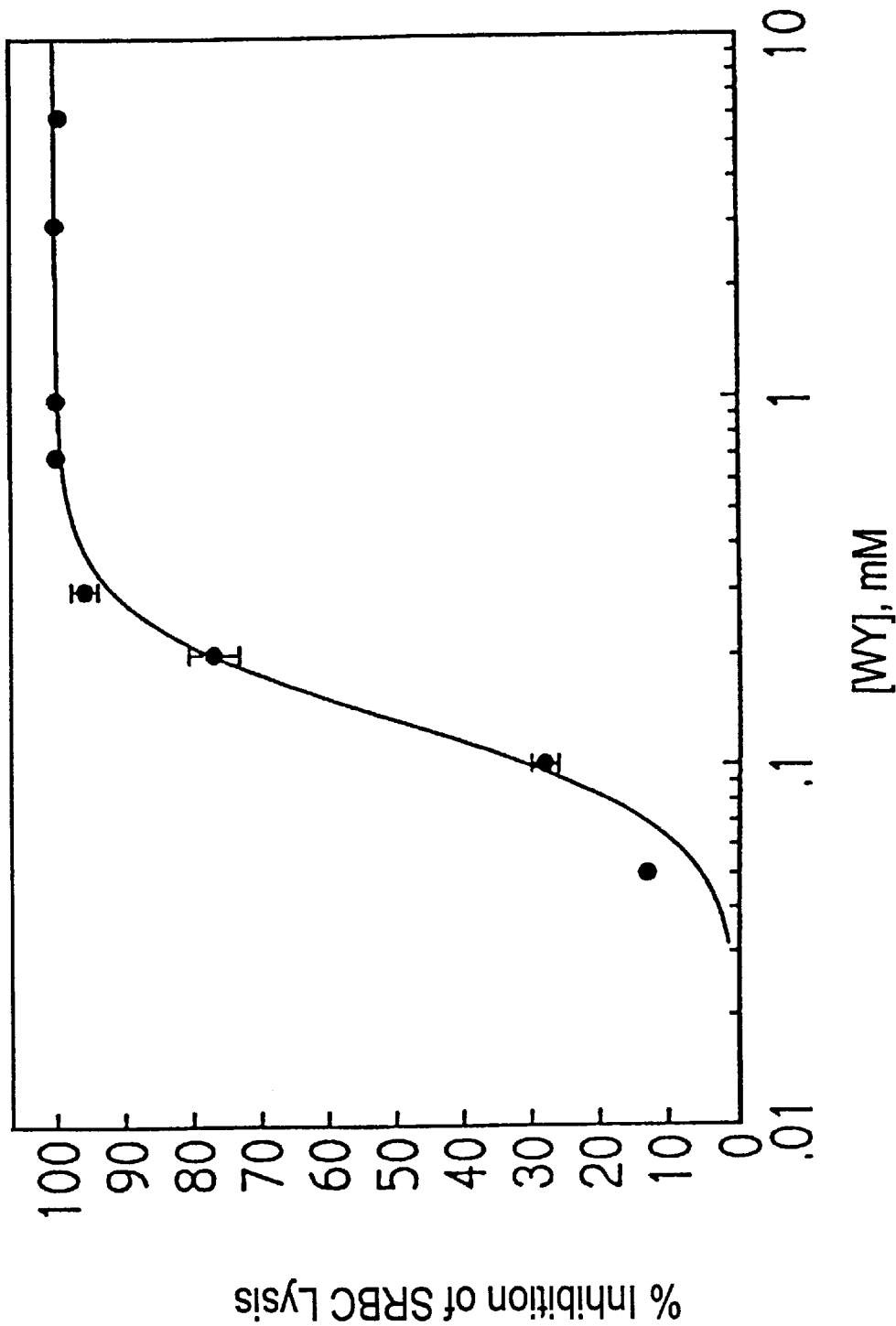
FIG. 4. Graph of inhibition of SRBC lysis versus concentration of Trp-Tyr ([WY]) in Trp-Tyr-BSA conjugates. The data points ±SD values of three different preparations of Trp-Tyr-BSA of similar activities were combined and plotted.
Figure 5:
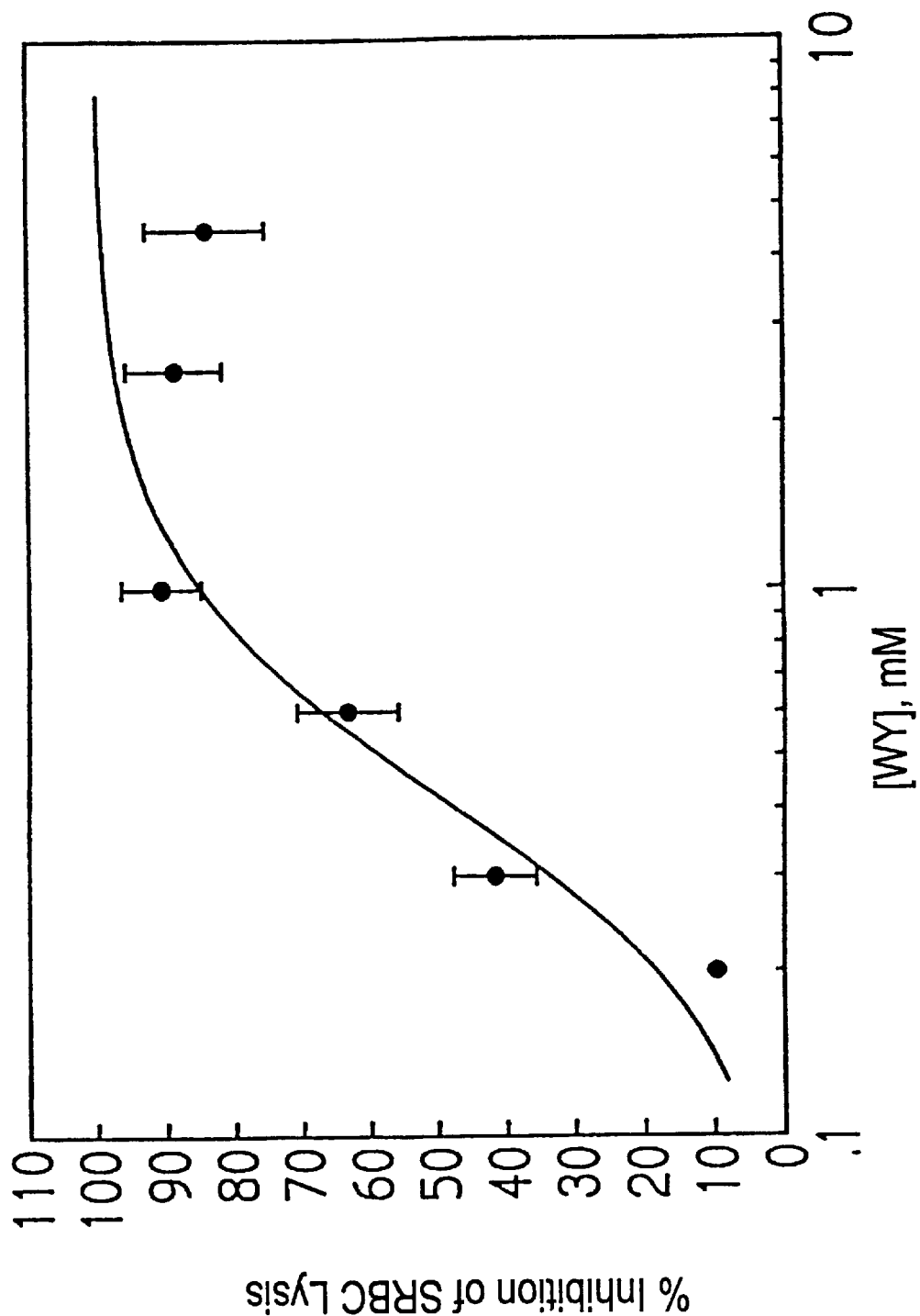
FIG. 5. Graph of inhibition of SRBC lysis versus concentration of Trp-Tyr ([WY]) in the Trp-Tyr-BSA conjugates. The data points ±SD values of three additional different preparations of Trp-Tyr-BSA of similar activities were combined and plotted.

Using weight ratios of Trp-Tyr:BSA of 1:1, 2:1 and 4:1 yielded conjugates with IC50 values (inhibitory concentration giving 50% inhibition) of about 2, 0.75 and 0.25 mg Trp-Tyr-BSA/ml, respectively, in the SRBC lysis assay. See FIGS. 2A–B. On the basis of the Trp-Tyr concentrations of the Trp-Tyr-BSA conjugates, concentrations between 0.14 and 0.18 mM Trp-Tyr gave 50% inhibition of complement activation. Because the objective was to achieve nearly complete complement inhibition, the condition of Trp-Tyr:BSA of 2:1 was chosen for subsequent preparations as both conditions of Trp-Tyr:BSA of 2:1 and 4:1 yielded Trp-Tyr-BSAs with essentially identical concentrations yielding nearly 100% inhibitions (1.8 mg/ml Trp-Tyr-BSA). An example of the results obtained with a Trp-Tyr-BSA conjugate prepared with Trp-Tyr:BSA ratio of 2:1 is shown in FIGS. 3A–B. IC50 was obtained with a Trp-Tyr-BSA concentration of 0.12 mg/ml, corresponding to a Trp-Tyr concentration of 0.18 mM. The Trp-Tyr-BSA conjugates varied in complement inhibitory activities as shown for six different preparations giving IC50 values in terms of Trp-Tyr concentrations between 0.13 and 0.30 mM (FIGS. 4 and 5).

Figure 6:
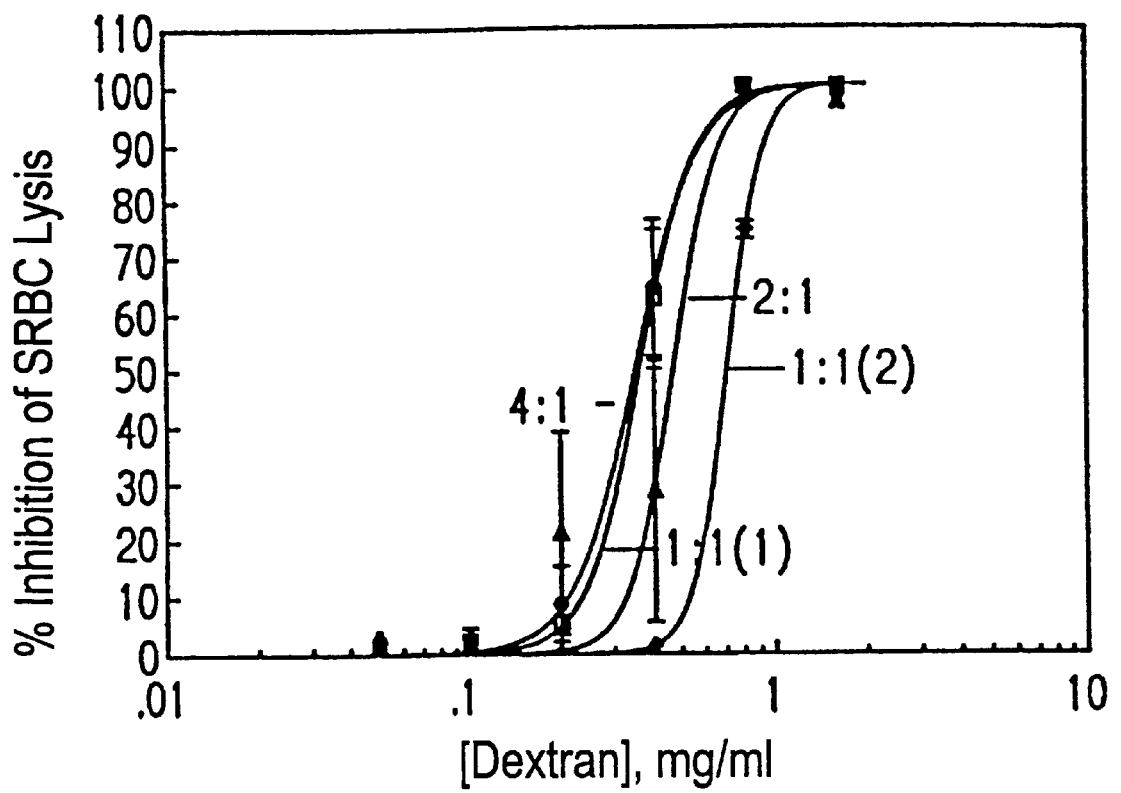
FIGS. 6A–B. Graphs of inhibition of SRBC lysis using Trp-Tyr conjugated to dextran of molecular weight 500,000 using weight ratios of 1:1, 2:1, and 4:1 Trp-Tyr:dextran in the reductive amination step. Inhibition is plotted versus concentration of Trp-Tyr-Dextran ([Dextran]) (FIG. 6A) and versus concentration of Trp-Tyr ([WY]) in the Trp-Tyr-Dextran conjugates (FIG. 6B). Two separate 1:1 preparations are plotted, (1) and (2). The data points ±SD values are the averages from 2 experiments performed at different times.
Figure 6:
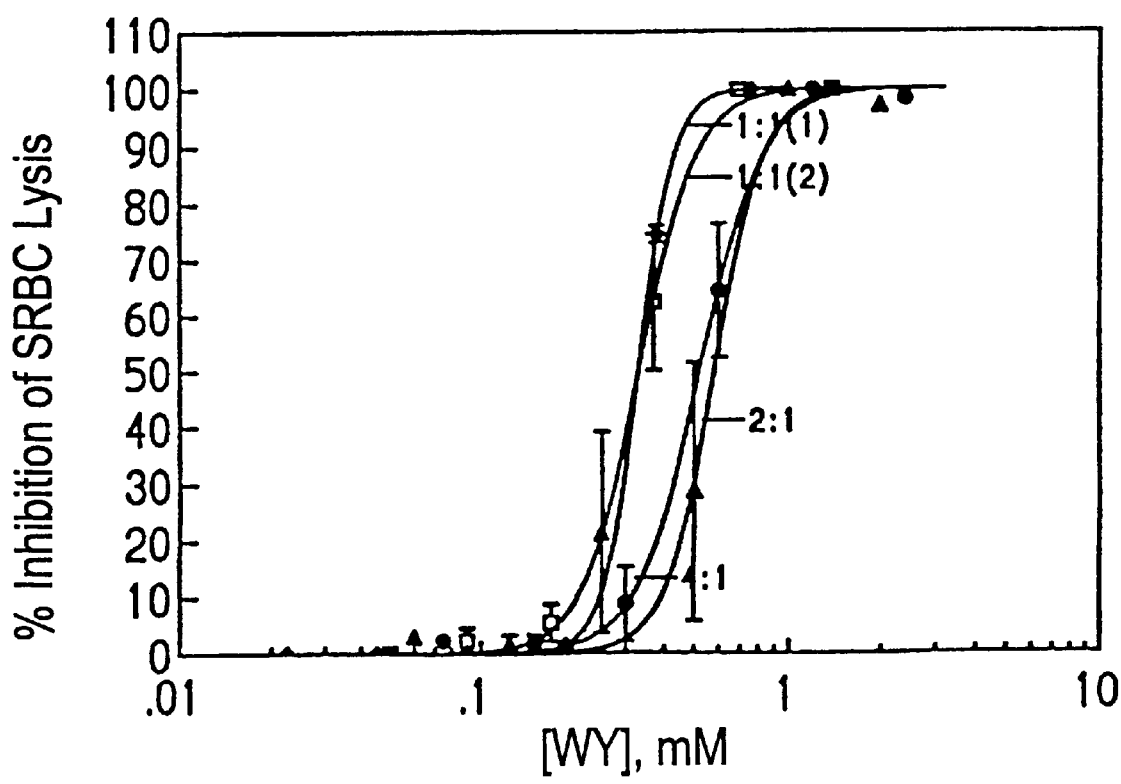
Figure 7:
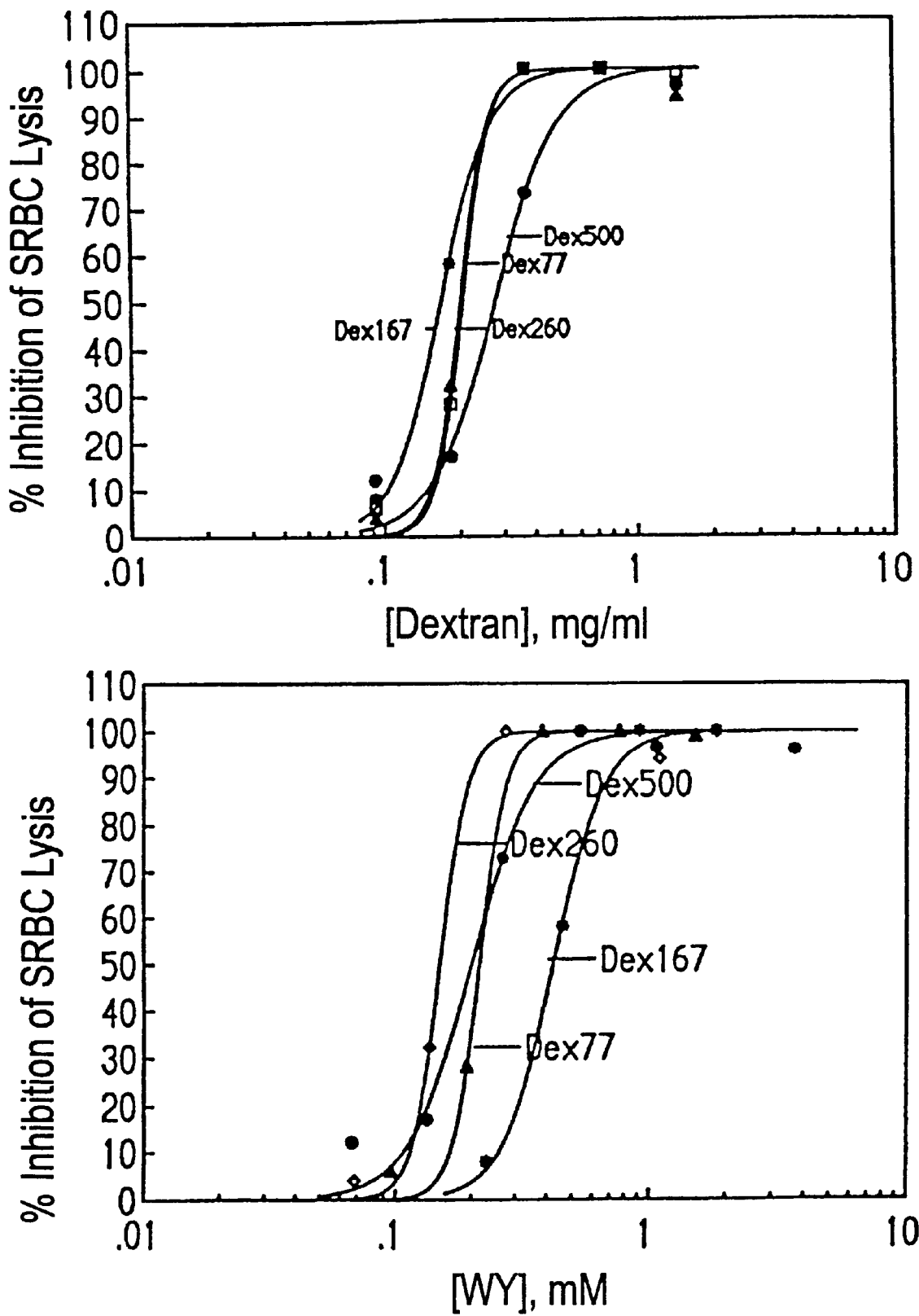
FIGS. 7A–B. Graphs of inhibition of SRBC lysis using Trp-Tyr conjugated to dextrans of various molecular weights. Inhibition is plotted against concentration of Trp-Tyr-Dextran ([Dextran]) (FIG. 7A) and against concentration of Trp-Tyr ([WY]) in the Trp-Tyr-Dextran conjugates (FIG. 7B) The data points are the averages of duplicates of a single experiment. Dex77, Trp-Tyr-Dextran 77,000; Dex 167, Trp-Tyr-Dextran 167,000; Dex 260, Trp-Tyr-Dextran 260,000; Dex 500, Trp-Tyr-Dextran 500,000.
Figure 8:
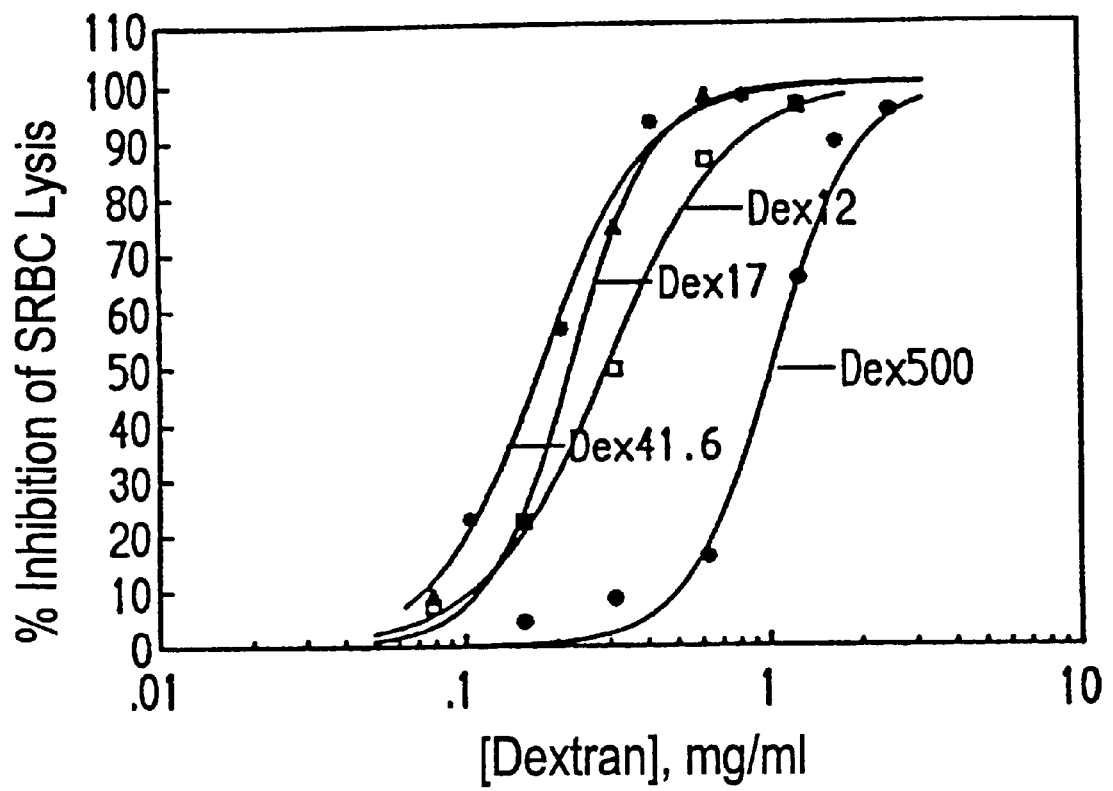
FIGS. 8A–B. Graphs of inhibition of SRBC lysis using Trp-Tyr conjugated to dextrans of various molecular weights. Inhibition is plotted against concentration of Trp-Tyr-Dextran ([Dextran]) (FIG. 8A) and against concentration of Trp-Tyr ([WY]) in the Trp-Tyr-Dextran conjugates (FIG. 8B). The data points are the averages of duplicates of a single experiment. Dex 12, Trp-Tyr-Dextran 12,000; Dex 17, Trp-Tyr-Dextran 17,000; Dex 41.6, Trp-Tyr-Dextran 41,600; Dex 500, Trp-Tyr-Dextran 500,000.
Figure 8:
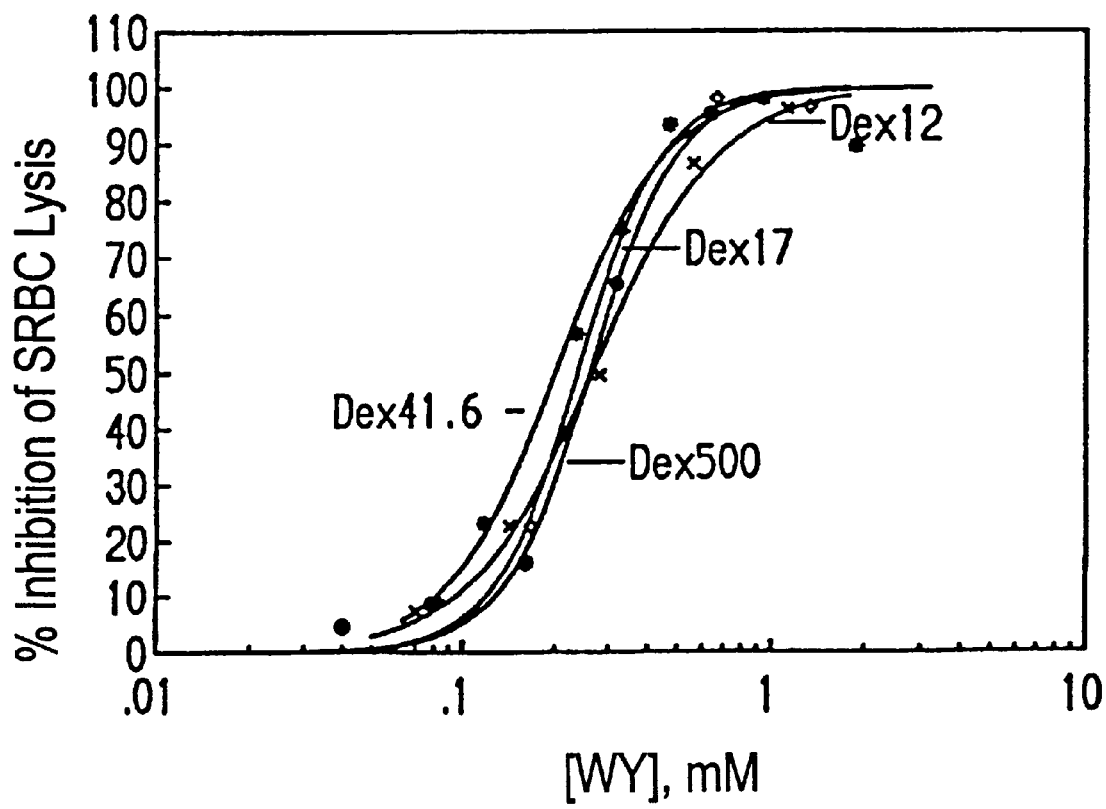

Conjugates of the diaromatic Trp-Tyr peptide were also made with dextrans of sizes ranging from 12,000 to 500,000 daltons average molecular weights. The amounts of periodate to dextran in the oxidation reaction was studied and using weight ratios of less than 4:1 of periodate:dextran was found to yield conjugates with much less activity. The ratios of Trp-Tyr to dextran in the reductive amination reaction were also studied. Using weight ratios of Trp-Tyr:Dextran of 4:1, 2:1, 1:1, 1:2 and 1:3 in the conjugation reaction yielded conjugates with 740, 620, 427, 234 and 46 Trp-Tyr dipeptide residues, respectively, per dextran molecule of 500,000 daltons average molecular weight and having 4.17, 4.98, 7.22, 13.2 and 67.2 glucose residues of the dextran per Trp-Tyr dipeptide, respectively. When Trp-Tyr:Dextran ratios were less than 1:1, conjugates of low activity were obtained. Using ratios of 1:1, 2:1 and 4:1 of Trp-Tyr to dextran yielded conjugates with complement inhibitory activities (IC50) in the range of 0.25–0.55 mg/ml Trp-Tyr-dextran, corresponding to 0.2–0.5 mM Trp-Tyr concentration in the conjugates (FIGS. 6A–B).

Trp-Tyr was conjugated to dextrans of different sizes and their complement inhibitory activities in the SRBC lysis assay determined as shown in FIGS. 7A–B and 8A–B. For dextrans of 77,000, 167,000 and 260,000 plus the 500,000 average molecular weights, IC50 values were between 0.15 and 0.3 mg/ml of Trp-Tyr-Dextrans and between 0.15 and 0.42 mM Trp-Tyr concentrations in the conjugates. The dextrans of average molecular weights 12,000, 17,000 and 41,600 together with the 500,000 yielded IC50 values between 0.13 and 1 mg/ml Trp-Tyr-Dextran and 0.18–0.28 mM Trp-Tyr concentrations in the conjugates.

Figure 9:
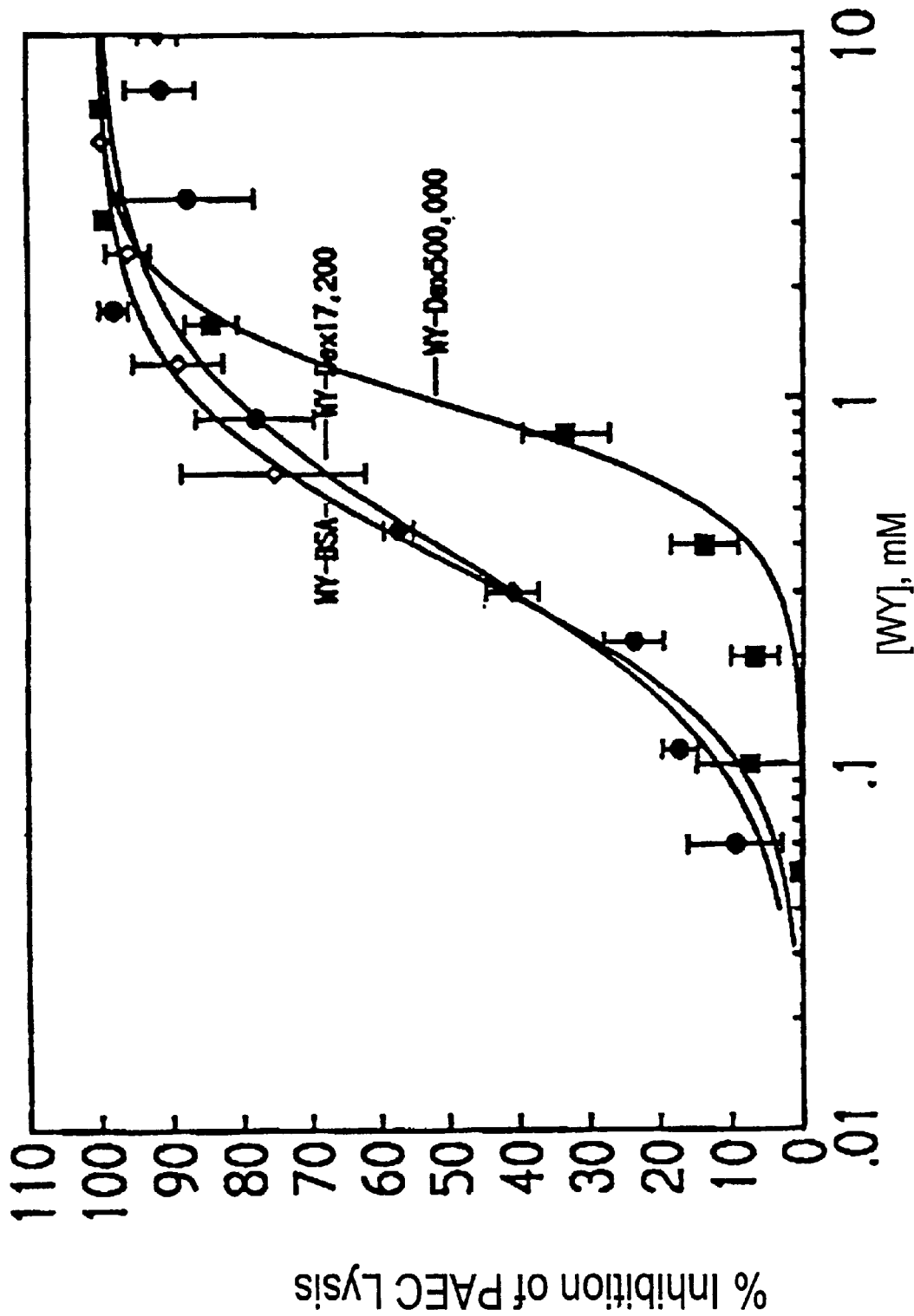
FIG. 9. Graph of inhibition of pig aorta endothelial cell (PAEC) lysis using Trp-Tyr-BSA (WY-BSA, ◇), Trp-Tyr-DEXTRAN (WY-Dex 17,200, ●, dextran of 17,200 daltons average molecular weight) and Trp-Tyr-Dextran (WY-Dex 500,000, ■, dextran of 500,000 daltons average molecular weight) conjugates versus concentration of Trp-Tyr ([WY]) in the conjugates. The data points are the average of triplicate values of a single experiment ±SD.

Trp-Tyr-BSA and Trp-Tyr-Dextran conjugates also effectively inhibited the lysis of pig endothelial cultured cells mediated by anti-porcine endothelial cell antibody and complement from human serum (FIG. 9). Using the Trp-Tyr-BSA and Trp-Tyr-Dextran 17,200 conjugates, approximately 50% inhibition of cell lysis was obtained with 0.35 mM Trp-Try concentration of the conjugates and nearly complete inhibition of cell lysis was seen at the 1.1 mM Trp-Tyr concentration. For the Trp-Tyr-Dextran 500,000 conjugate, 50% and 100% inhibition were obtained at about 1 and 3 mM, respectively, Trp-Tyr concentration in the conjugate.

In conclusion, it can be readily seen from a comparison of the IC50 values in the SRBC lysis assay for the Trp-Tyr-BSA conjugates (0.13 mM to 0.30 mM) and Trp-Tyr-Dextran conjugates (0.15 mM to 0.50 mM) compared to Trp-Tyr alone (15 mM), that up to a 115-fold increase (range of about 30–115 fold increase) in complement inhibitory activity was achieved in terms of Trp-Tyr concentration using the Trp-Tyr-Carrier conjugates. Without wishing to be bound by any theory, it is speculated that the multiple Trp-Tyr diaromatic peptides of the conjugates form more than one binding interaction with more than one of the immunoglobulin binding sites of the six globular head regions of C1q.

Furthermore, complete inhibition of complement activation was achieved with as little as 0.2–0.4 mg/ml of Trp-Tyr-Dextran or Trp-Tyr-BSA. Such concentrations would correspond to between 1000 and 2000 mg of Trp-Tyr-Carrier in a human with a 5 liter blood volume. These amounts of Trp-Tyr-Carrier are reasonable to administer a human prior to and/or after a transplant procedure in order to suppress rejection caused by complement activation or through rejection mechanisms involving C1q receptors. Furthermore, at a 1 mg/ml concentration of Trp-Tyr-BSA, nearly complete inhibition of porcine endothelial cell lysis was achieved (FIG. 9) as mediated by human antibody and complement reactions, the type of rejection responses that would occur if a pig organ were to be transplanted into a human.

Example 2
Trp-Tyr-BSA Prolongs Graft Survival of Heterotropic Heart Transplantation Four to six week old guinea pig (GP, Harlan, Indianapolis, Ind.) hearts were transplanted into C6 deficient PVG rats (B & K, Kent, Wash.) by the technique of Ono and Lindsay (*J. Thoracic Cardiovascular Surgery*, 57, 225, 1969). Eighteen rats served as controls and received intravenous injections of PBS only and were fitted subdermally with model 2ML1 ALZET osmotic pumps (ALZA Corp., Palo Alto, Calif., mean pumping rate of 10 $\mu$l/hour) filled with 2.3 ml of PBS. The intravenous injection was given and the pumps were fitted 24 hours before transplant. Eight rats received a 0.5–1.0 ml intravenous injection of Trp-Tyr-BSA in PBS to yield a concentration in the blood of the rat of 0.8–1.2 mM Trp-Tyr of the Trp-Tyr-BSA conjugate (assuming a 10 ml blood volume of the rat). The rats were also fitted with the ALZET pumps filled with a Trp-Tyr-BSA solution in PBS 24 hours before transplant. It was calculated that the solution delivery rate of the ALZET pump would maintain a blood concentation in the rat of 0.1 mM in terms of the Trp-Tyr concentration of the Trp-Tyr-BSA conjugate. The Trp-Tyr-BSA was prepared as described in Example 1 using a Trp-Tyr:BSA ratio of 2:1.

The Trp-Tyr-BSA conjugate prolonged graft survival of the GP heart transplanted to the C6 deficient PVG rat (Table 1). Treatment of the rats with the Trp-Tyr-BSA increased the GP heart survival to 2.4±0.7 days from 1.4±0.5 days for the control animals (no treatment)(p=0.009). The Trp-Tyr-BSA preparations used in these animal experiments yielded IC50 values in the SRBC lysis assay in the range of 0.075 to 0.25 mg/ml Trp-Tyr-BSA and 0.22 to 0.5 mM Trp-Tyr concentration of the Trp-Tyr-BSA conjugate. Assuming a blood volume of approximately 10 ml for the rats, the concentration of Trp-Tyr of the Trp-Tyr-BSA in the blood of the rat from the intravenous injection was calculated to range between 3 and 4.5 mM and the osmotic pumps would deliver a concentration of Trp-Tyr in the blood of 0.03 to 0.045 mM per hour. Because the clearance and the body distribution of the amounts of Trp-Tyr-BSA from the intravenous injections and pumps were not determined, the blood levels of Trp-Tyr-BSA are not known.

TABLE 1

Graft Survival of Guinea Pig Hearts Transplanted into C6 Deficient PVG Rats

| Treatment | Number of Rats | Mean Graft Survival, days, average + SD | p Value |
|---|---|---|---|
| PBS controls | 18 | 1.4 ± 0.5 | |
| Trp-Tyr-BSA treated | 8 | 2.4 ± 0.7 | 0.009 vs. controls |

Figure 10:
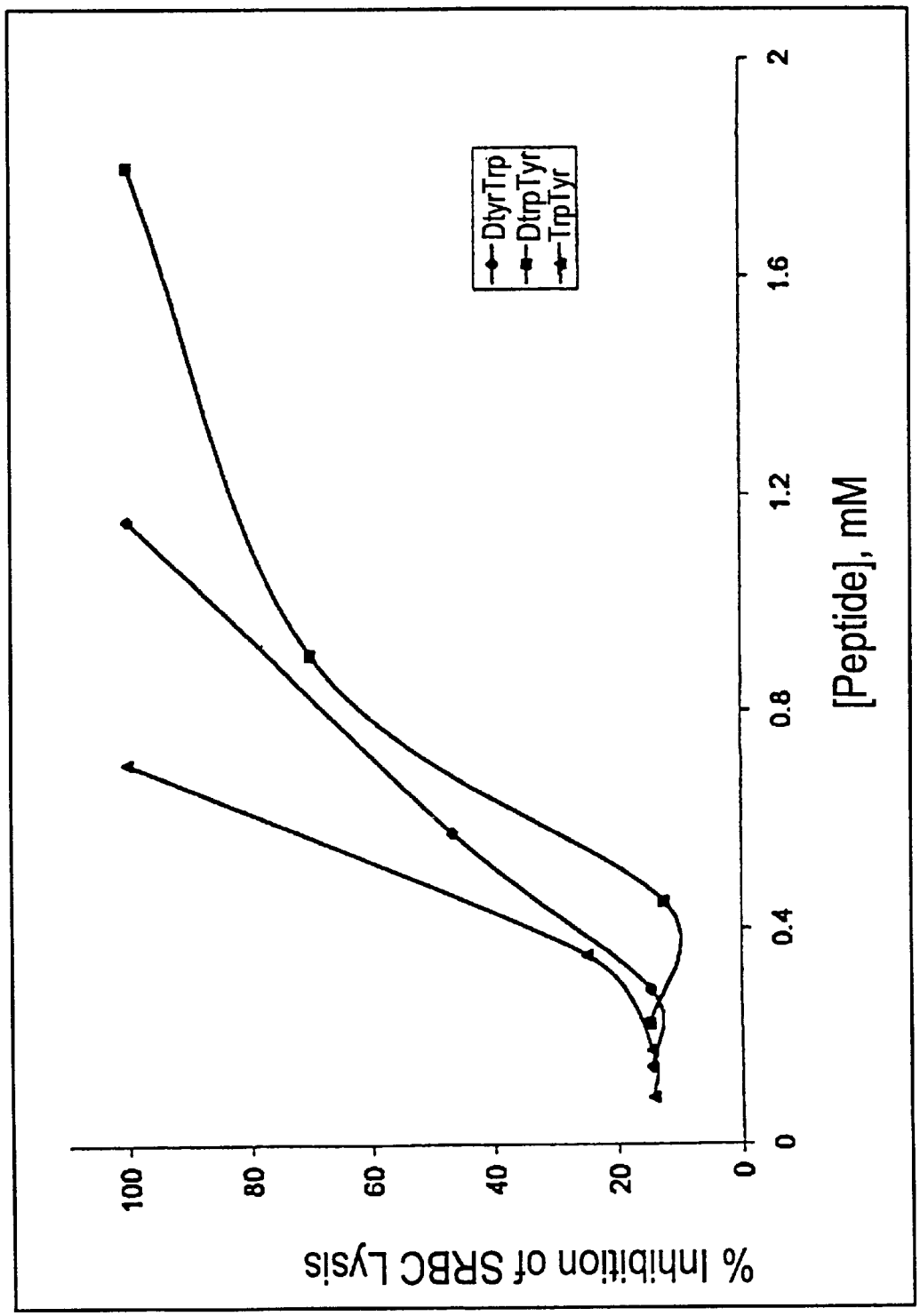
FIG. 10. Graph of inhibition of SRBC lysis using (L)Trp-(L)Tyr (▲), (D)Trp-(D)Tyr (■) and (D)Tyr-(D)Trp (♦) conjugated to dextran (average molecular weight of 12,000 daltons). Inhibition is plotted against concentration of dipeptide ([Peptide]).

Example 3
Inhibition of Complement-Mediated Lysis By Additional Dextran Conjugates This example describes the inhibition of complement-mediated lysis using dipeptides containing D-amino acids or L-amino acids coupled to dextran (average molecular weight of 12,000 daltons). The coupling of the dipeptides to the dextran was accomplished as described in Example 1. The dipeptides containing D-amino acids were synthesized by Peptides International (Louisville, Ky.). (L)Trp-(L)Tyr was obtained from Bachem Biosciences, Inc. (King of Prussia, Pa.). The dipeptide-dextran conjugates were tested in the SRBC lysis assay performed as described in Example 1. The results are shown in FIG. 10. As can be seen, all three dipeptide-dextran conjugates inhibited SRBC lysis at low dipeptide concentrations, yielding IC50 values of approximately 0.4, 0.55 and 0.65 mM dipeptide concentration in the (L)Trp-(L)Tyr, (D)Tyr-(D)Trp, and (D)Trp-(D)Tyr conjugates, respectively.

Figure 11:
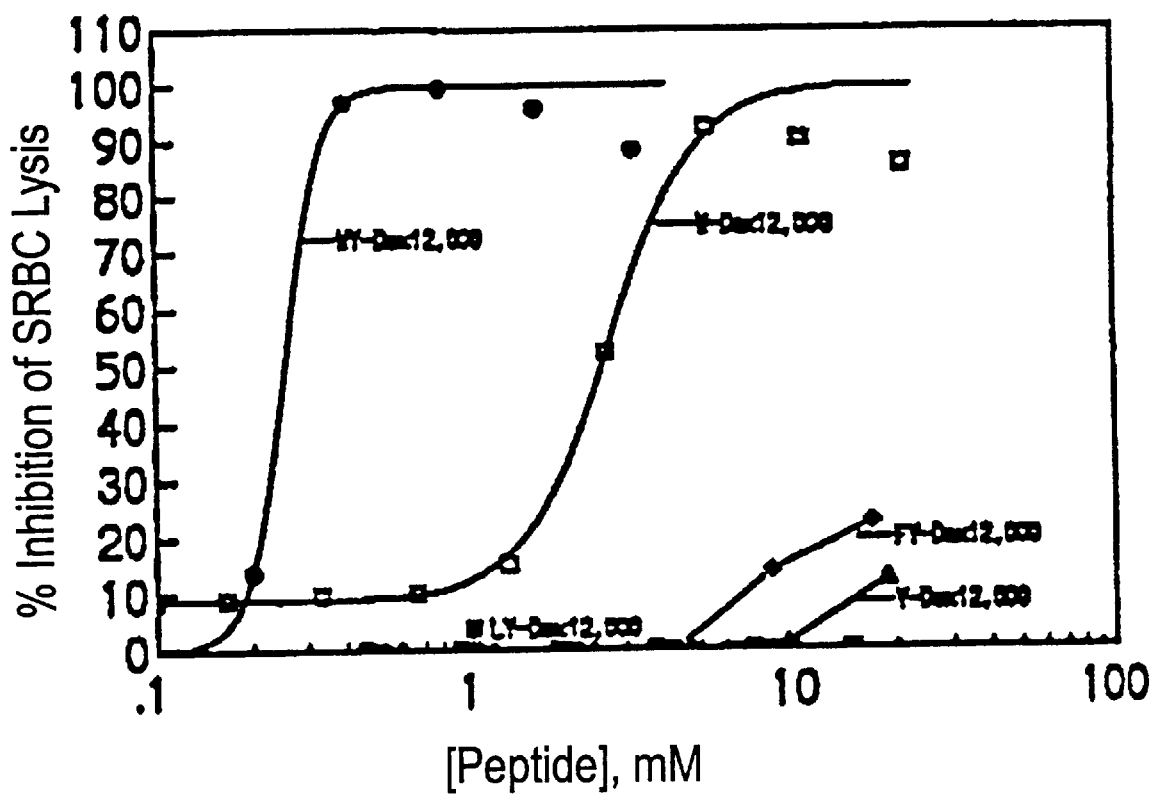
FIG. 11. Graph of inhibition of SRBC lysis using Trp-Tyr-Dextran (WY-Dex, ●), Trp-Dextran (W-Dex, □), Tyr-Dextran (Y-Dex, ▲), Leu-Tyr-Dextran (LY-Dex, ■) and Phe-Tyr-Dextran (FY-Dex, ♦) (dextran in all cases having average molecular weight of 12,000 daltons). Inhibition is plotted against concentration of amino acid or dipeptide ([Peptide]). The data points are the average of duplicate values in a single experiment.

Several additional conjugates of dipeptides (containing L-amino acids) and of L-amino acids to dextran (average molecular weight of 12,000 daltons) were prepared as described in Example 1 (amino acids and dipeptides from Sigma Chemical Co., St. Louis, Mo.). The amino acids and dipeptides included: Trp, Tyr, Leu-Tyr, Phe-Tyr, Trp-Ala, Trp-Glu, Trp-Leu, Trp-Phe, Tyr-Tyr, Tyr-Val, Tyr-Phe, Ala-Tyr, Glu-Tyr, Ser-Tyr, His-Tyr, Val-Tyr and Gly-Tyr. These additional conjugates were tested compared to Trp-Tyr-Dextran in the SRBC lysis assay as described in Example 1. Some of the results are presented in FIG. 11. Of the conjugates tested, Trp-Dextran exhibited the greatest inhibition, being approximately 20-fold less active than Trp-Tyr-Dextran (see FIG. 11).

We claim:

1. A pharmaceutical composition comprising a carrier, the carrier having a plurality of dipeptides coupled to it, the dipeptides being selected from the group consisting of tryptophan-tyrosine, tyrosine-tryptophan, tryptophan—tryptophan, and combinations thereof, provided that if the carrier is a peptide or protein, at least one of said dipeptides is coupled to a side chain of an amino acid contained within the peptide or protein; together with a pharmaceutically-acceptable vehicle.

2. The composition of claim 1 wherein the dipeptides are tryptophan-tyrosine.

3. The composition of claim 1 wherein the carrier is bovine serum albumin.

4. The composition of claim 1 wherein the carrier is dextran.

5. The composition of claim 1 wherein the dipeptides are tyrosine-tryptophan.

6. The composition of claim 1 wherein the dipeptides are tryptophan—tryptophan.

7. The composition of claim 3 wherein each molecule of bovine serum albumin has on average at least about forty dipeptides coupled to it.

8. The composition of claim 4 wherein each molecule of dextran has on average at least about four hundred dipeptides coupled to it.

* * * * *